United States Patent
Satake

(10) Patent No.: US 7,112,198 B2
(45) Date of Patent: Sep. 26, 2006

(54) RADIO-FREQUENCY HEATING BALLOON CATHETER

(76) Inventor: Shutaro Satake, 4-8-18, Kamakurayama, Kamakura-Shi, Kanagawa-Ken (JP)

( * ) Notice: Subject to any disclaimer, the term of this patent is extended or adjusted under 35 U.S.C. 154(b) by 340 days.

(21) Appl. No.: 10/747,301

(22) Filed: Dec. 30, 2003

(65) Prior Publication Data

US 2004/0172110 A1    Sep. 2, 2004

(30) Foreign Application Priority Data

Jan. 24, 2003   (JP)  ............................. 2003-016504

(51) Int. Cl.
*A61B 18/14* (2006.01)
(52) U.S. Cl. .......................... 606/41; 606/49
(58) Field of Classification Search ............ 606/41
See application file for complete search history.

(56) References Cited

U.S. PATENT DOCUMENTS

| 2002/0029062 | A1 | 3/2002 | Satake |
| 2002/0165535 | A1* | 11/2002 | Lesh et al. ................. 606/41 |
| 2004/0147915 | A1* | 7/2004 | Hasebe ....................... 606/28 |

FOREIGN PATENT DOCUMENTS

| EP | 1297795 | | 4/2003 |
| WO | 96/15741 | * | 5/1996 |
| WO | 02/19934 | | 3/2002 |
| WO | 2004/017850 | | 3/2004 |

* cited by examiner

*Primary Examiner*—Lee S. Cohen
(74) *Attorney, Agent, or Firm*—Wenderoth, Lind & Ponack, L.L.P.

(57) ABSTRACT

A radio-frequency heating balloon catheter is capable of cauterizing a target lesion in an atrial vestibule. The radio-frequency heating balloon catheter has a catheter tube including an outer tube and an inner tube slidably extended through the outer tube. An inflatable balloon is connected to an extremity of the outer tube and a part near an extremity of the inner tube, and is capable of coming into contact with a target lesion when inflated. A radio-frequency electrode serves as a counter to a surface electrode attached to a surface of a subject's body and is placed in a wall of the balloon or inside the balloon to supply radio-frequency power between the surface electrode and the radio-frequency electrode. A temperature sensor senses temperature inside the balloon, a guide shaft projects from the extremity of the inner tube and is capable of holding the balloon on the target lesion, and a guide wire extends through the catheter tube and the guide shaft.

14 Claims, 10 Drawing Sheets

RADIO-FREQUENCY HEATING BALLOON CATHETER

BACKGROUND OF THE INVENTION

1. Field of the Invention

The present invention relates to a radio-frequency heating balloon catheter and, more particularly, to a radio-frequency balloon catheter for the radio-frequency heating treatment of cardiovascular diseases. More specifically, the present invention relates to a radio-frequency heating balloon catheter provided with a balloon to be brought into close contact with a target lesion for radio-frequency heating for the treatment of cardiac arrhythmia.

2. Description of the Related Art

A known method of electrically coagulating a source of arrhythmia (catheter ablation) uses a catheter provided with a metal tip of 4 mm in size, which serves as an electrode, brings the metal tip into contact with the source of arrhythmia and supplies a radio-frequency current to the metal tip. Although this method is effective when the source is a local, one like a source of WPW syndrome or paroxysmal tachycardia, the method is not so effective when the source is an extensive one like a source of atrial fibrillation, atrial flutter or ventricular tachycardia due to organic heart diseases.

Another method of isolating a wide target part heats the target part electrically by radio-frequency heating using an inflatable balloon. Methods of treating lesions caused by arteriosclerosis as well as sources of arrhythmia proposed in, for example, Jpn. Pat. Nos. 2538375, 2510428 and 2574119 to the applicant of the present invention patent application treat a lesion by bringing an inflatable balloon internally provided with a radio-frequency electrode into contact with tissues, and creating a radio-frequency electric field to heat tissues in contact with the balloon.

The interior of the atrium needs to be cauterized linearly to treat atrial flutter or atrial fibrillation.

It has hitherto been believed that the superior pulmonary veins and the inferior pulmonary veins connected to the left atrium are separated and those four pulmonary veins open individually into the left atrium as shown in FIG. 9 or 10. In forming a block line by linearly cauterizing the interior of the atrium to treat atrial flutter or atrial fibrillation, the edges of the four ostia, i.e., the superior right, the superior left, the inferior right and the inferior left opening, of the pulmonary veins must individually be cauterized. A ablation for individually cauterizing the edges of the four ostia of the pulmonary veins takes much time. Since the thin wall of the pulmonary vein is liable to contract and, consequently, the stenosis of the pulmonary vein is liable to occur when the periphery of the pulmonary vein is cauterized.

SUMMARY OF THE INVENTION

Accordingly, it is an object of the present invention to provide a radio-frequency heating balloon catheter capable of making the individual cauterization of the edges of the four pulmonary vein openings unnecessary and of capable of cauterizing a wide range of the atrial vestibule where the pulmonary veins join together with a balloon kept in a coaxial state.

Recently, the inventors of the present invention have found that the superior and the inferior pulmonary vein are not separately connected to the atrium, the superior and the inferior pulmonary vein join together and form an atrial vestibule before the atrium, and the atrial vestibule opens into the atrial body. The left superior pulmonary vein 101 and the left inferior pulmonary vein 102 join at the left atrial vestibule 103, and the right superior pulmonary vein 105 and the right inferior pulmonary vein 106 join at the right atrial vestibule.

According to the findings of the inventors of the present invention, the two pulmonary veins, i.e., the superior and the inferior pulmonary vein, join at the atrial vestibule before the atrial body, do not open individually into the atrial body, and the atrial vestibule opens into the atrial body.

The present invention has been made on the basis of the foregoing knowledge acquired by the inventors of the present invention.

According to the present invention, a radio-frequency heating balloon catheter comprises: a catheter tube including an outer tube and an inner tube slidably extended through the outer tube. An inflatable balloon is connected to the extremity of the outer tube and a part near the extremity of the inner tube, and is capable of coming into contact with a target lesion when inflated. A radio-frequency electrode serving as a counter to a surface electrode attached to the surface of a subject's body and is placed in the wall of the balloon or inside the balloon to supply radio-frequency power between the surface electrode and the radio-frequency electrode. A temperature sensor capable of measuring temperature inside the balloon, a guide shaft projecting from the extremity of the inner tube and is capable of holding the balloon on the target lesion, and a guide wire extended through the catheter tube and the guide shaft.

In the radio-frequency heating balloon catheter, the guide shaft may be capable of holding the balloon on the target lesion.

In the radio-frequency heating balloon catheter, the guide shaft may be formed of a nonconductive material having a low heat conductivity.

In the radio-frequency heating balloon catheter, the guide shaft and the inner tube may be formed integrally and coaxially of the same material.

In the radio-frequency heating balloon catheter, the balloon may be formed of a heat-resistant, antithrombotic, elastic material, and may be formed in a shape such that the balloon is able to come into contact with an atrial vestibule at the junction between the superio and the inferior pulmonary vein when inflated.

In the radio-frequency heating balloon catheter, the guide shaft may have a length such that a side surface of the guide shaft is able to come into contact with the superior or the inferior pulmonary vein with the inflated balloon in contact with the atrial vestibule.

In the radio-frequency heating balloon catheter, the shape of the balloon capable of coming into contact with the atrial vestibule when inflated is determined on the basis of data obtained by scanning the atrial vestibule by three-dimensional CT before executing a ablation.

In the radio-frequency heating balloon catheter, the guide shaft may have a length longer than that of the balloon.

In the radio-frequency heating balloon catheter, the guide shaft may have a length between 1 and 10 cm.

In the radio-frequency heating balloon catheter, a free end part of the inner tube or the guide shaft may be provided with side holes to suck blood in the pulmonary vein.

In the radio-frequency heating balloon catheter, the back end of the guide wire may be able to be grounded.

The radio-frequency heating balloon catheter may further comprise a temperature-distribution uniforming means for making uniform temperature distribution in a liquid contained in the balloon.

The radio-frequency heating balloon catheter may further comprise a cooling means for cooling the radio-frequency electrode.

According to the present invention, the atrial vestibule where the superior and the inferior pulmonary vein join can be cauterized instead of individually cauterizing the edges of the ostia of the superior and the inferior pulmonary vein to form a block line by linearly cauterizing the interior of the atrium to treat atrial flutter or atrial fibrillation. Consequently, the edges of the four pulmonary vein ostia do not need to be individually cauterized, the number of parts to be cauterized is reduced and thereby time necessary for the ablation can be reduced.

Since the wall of the atrial vestibule, as compared with the walls of the pulmonary veins, is considerably thick, the atrial vestibule does not contract easily when cauterized, and hence the stenosis of the atrial vestibule does not occur easily.

The modification of the posterior wall of the left atrium in cauterizing the atrial vestibule enhances the suppressive effect on the maintenance of atrial fibrillation because the maintenance of atrial fibrillation requires the substrate of the posterior wall of the atrium with considerable area, and the ablation of the atrial vestibule reduces the substrate of the back wall of the atrium.

Generally, the balloon in contact with the target lesion must be kept in a coaxial state to cauterize a necessary and sufficient region including the target lesion. When a conventional balloon catheter is used for cauterizing the atrial vestibule, a balloon is brought into close contact with a target lesion, a guide wire is projected from the extremity of an inner tube so that the tip of the guide wire comes into contact with the inner surface of the wall of the pulmonary vein to support the balloon by the guide wire, the balloon is held in close contact with the atrial vestibule, and the balloon is held in a coaxial state by keeping the guide wire in contact with the inner surface of the wall of the pulmonary vein. The size of the atrial vestibule, as compared with the size of the pulmonary vein opening, is large and hence the balloon must be considerably large and the radio-frequency power must be increased accordingly. The following problems arise when the conventional balloon catheter is used for cauterizing the atrial vestibule. The guide wire extending through the balloon is heated by a high-temperature liquid contained in the balloon by thermal conduction. The guide wire is heated at an excessively high temperature by radio-frequency heating due to electromagnetic coupling and thereby the inner surface of the wall of the pulmonary vein is cauterized. Since high radio-frequency power must be supplied, the radio-frequency electrode is heated at an excessively high temperature, and temperature is distributed unevenly in the balloon and non-uniform cauterization results.

The radio-frequency heating balloon catheter of the present invention is capable of safely cauterizing the atrial vestibule where the pulmonary veins joins with the balloon held in a coaxial state.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

The basic construction of a radio-frequency heating balloon catheter 1 in a first embodiment according to the present invention will be described with reference to FIG. 1. The radio-frequency heating balloon catheter 1 will be described as applied to the treatment of a lesion in the left atrial vestibule 103. Naturally, the radio-frequency heating balloon catheter 1 is applicable to the treatment of a lesion in the right atrial vestibule.

Figure 1:
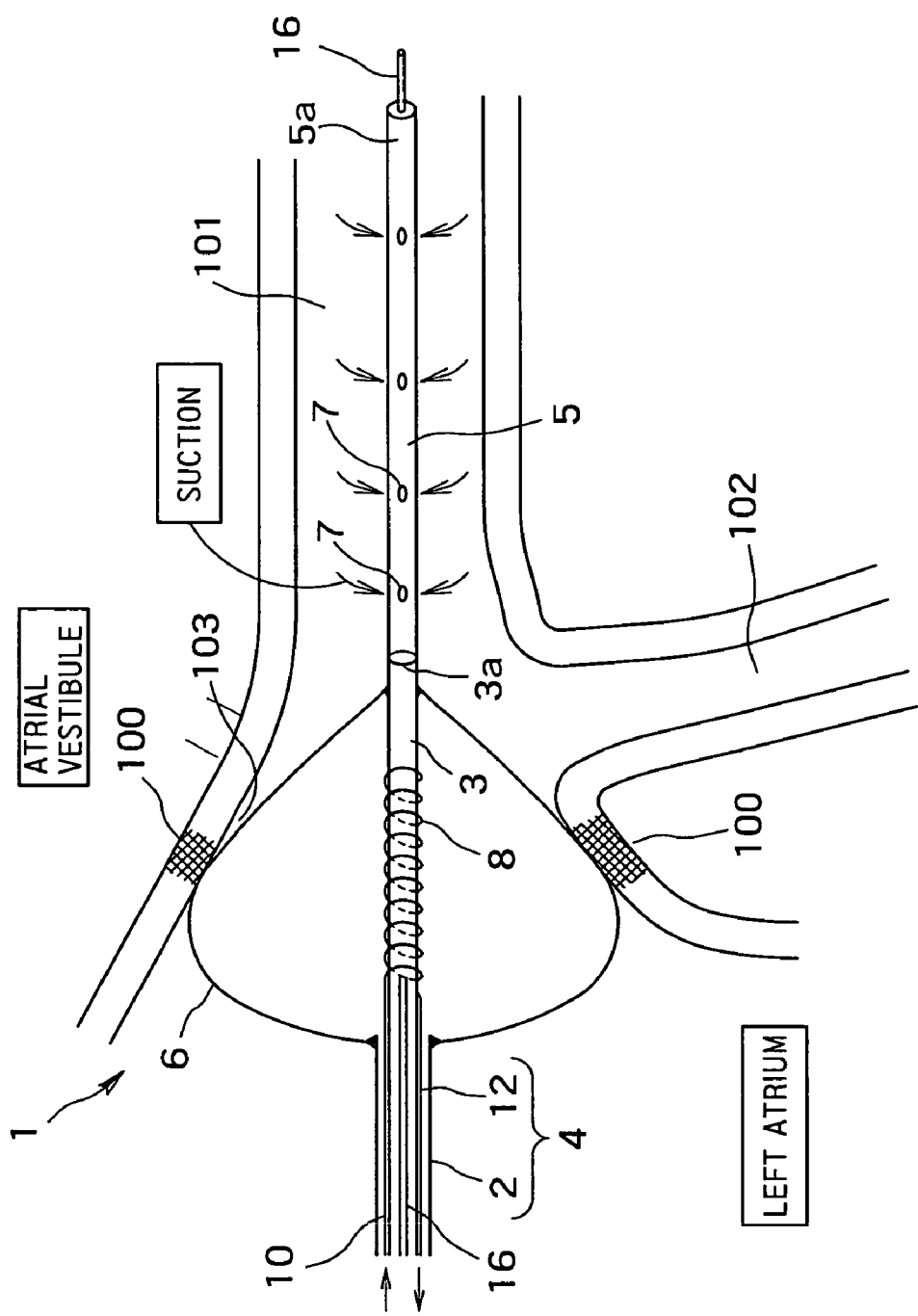
FIG. 1 is a view of a part of a radio-frequency heating balloon catheter in a first embodiment according to the present invention.

Referring to FIG. 1, the radio-frequency heating balloon catheter 1 comprises a catheter tube 4 including an outer tube 2 and an inner tube 3 slidable relative to the outer tube 2, an inflatable balloon 6 of a shape capable of coming into contact with a target lesion 100 in the left atrial vestibule 103 when inflated, a radio-frequency electrode 8 disposed inside the balloon 6, a lead wire 10 electrically connected to the radio-frequency electrode 8, a thermocouple 12 placed in the balloon 6 to sense temperature in the balloon 6, a guide shaft 5 extending from a front end part 3a of the inner tube 3 and capable of holding the balloon 6 on the target lesion 100, and a guide wire 16 extended through the catheter tube 4 and the guide shaft 5 to guide the catheter tube 4 and the guide shaft 5 to the target lesion 100.

The guide shaft 5 is formed of a nonconductive material having a low thermal conductivity, such as a resin, to avoid the danger of excessively heating and electrifying the inner surface of the left superior pulmonary vein 101 when the guide shaft 5 touches the inner surface of the left superior pulmonary vein 101. For example, the inner tube 3 is 1 mm in outside diameter and the guide shaft 5 is 2 mm in outside diameter. The inner tube and the guide shaft 5 may be formed of the same material or of different materials, respectively. The inner tube 3 and the guide shaft 5 may integrally be formed in a coaxial arrangement or may be formed separately.

The balloon 6 is formed in a size such that the inflated balloon 6 can come into contact with the open end of a left atrial vestibule 103 where the left superior pulmonary vein 101 and the left inferior pulmonary vein 102 join together. The diameter of the balloon 6 as inflated must be large to cauterize the target lesion 100 in the left atrial vestibule 103 having an open end greater than those of the pulmonary veins 101 and 102. Whereas the diameters of the conventional balloon are in the range of 10 to 15 mm, the diameter of the balloon 6 is, for example, in the range of 20 to 40 mm. The length of the balloon 6 is, for example, in the range of 20 to 30 mm. The balloon 6 is formed of a heat-resistant, antithrombotic, elastic resin. The balloon 6 shown in FIG. 1 has the shape of a basket or an onion when inflated.

Preferably, a balloon 6 is designed specially for a subject by the following procedure. The subject's atrial vestibule is scanned by a three-dimensional CT scanner prior to an ablation procedure. The shape and size of the balloon 6 are determined specially for the subject on the basis of information provided by the three-dimensional CT (computor tomography) scanner so that the balloon 6 as inflated can be in close contact with the subject's atrial vestibule.

Figure 2:
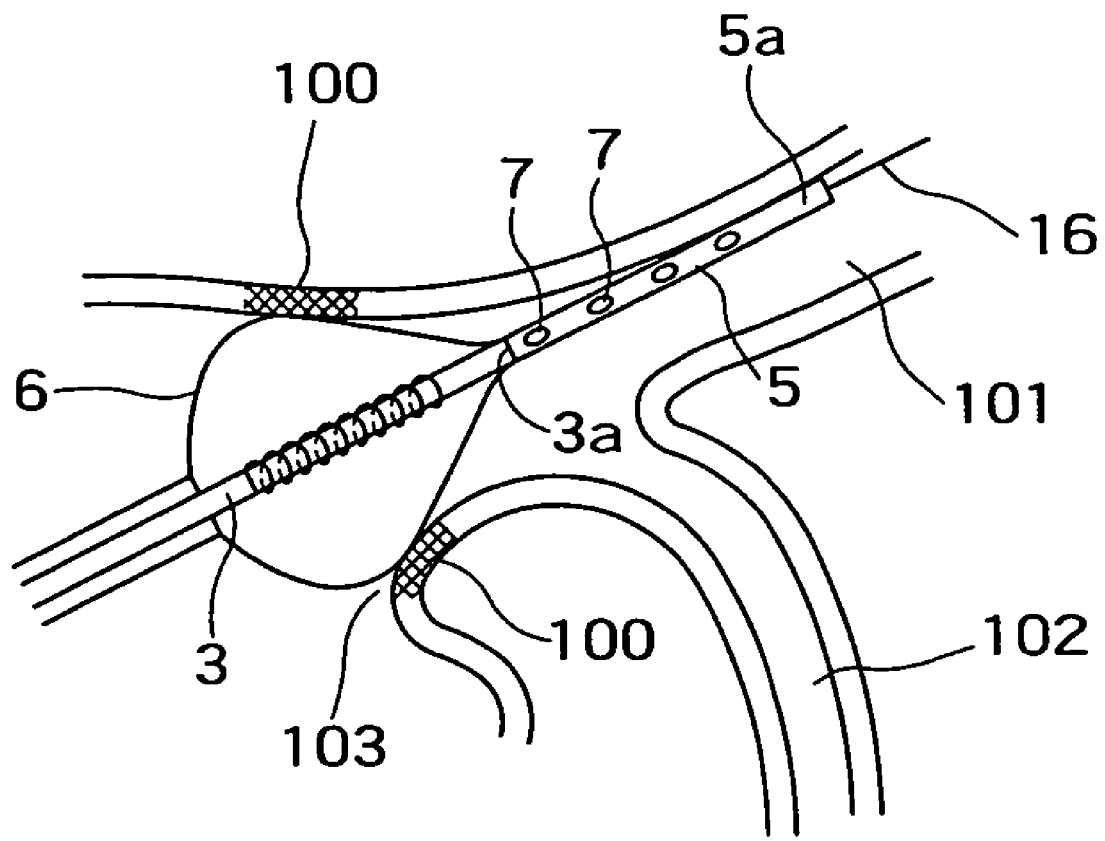
FIG. 2 is a view of the radio-frequency heating balloon catheter shown in FIG. 1 in a state where a balloon is in contact with an open part of an atrial vestibule and a side surface of a guide shaft is in contact with a part, near the open end of a pulmonary vein, of the inner surface of the wall of the pulmonary vein.

As shown in FIG. 2, the guide shaft 5 has a length such that the side surface 5a of the guide shaft 5 is able to be in contact with the inner surface of the wall of the left superior pulmonary vein 101 or the left inferior pulmonary vein 102 with the inflated balloon 6 in contact with the opening of the left atrial vestibule 103. The guide shaft 5 has a length longer than that of the balloon 6. For example, the length of the guide shaft 5 is between 2 and 10 cm.

The front end part 3a of the inner tube 3, or the guide shaft 5 is provided with side holes 7 through which pulmonary venous blood is sucked. The side holes 7 are used also for discharging physiological saline water into the left superior pulmonary vein 101.

The back end of the guide wire 16 can be connected to a ground. The back end is an end of the guide wire 16 opposite the front end of the same projecting from the guide shaft 5, and on the side of the inlet of the outer tube 2. The guide wire 16 is an insulated steel wire surrounded by an insulating material. The steel wire provides the guide wire 16 with rigidity, and the insulating material electrically insulates the steel wire. A back end part of the steel wire projecting from the back end of the guide wire 16 can be connected to the ground. A front end part of, for example, 1 cm in length projecting from the guide shaft 5 is formed only of the insulating material.

There is the possibility that Joul heat is generated in the steel wire of the guide wire 16 by a radio-frequency current. In the radio-frequency heating balloon catheter 1 in this embodiment having the large balloon 6 and using high power of radio-frequency power, it is possible that the guide wire 16 is heated at a high temperature. A radio-frequency current induced in the guide wire 16 can be discharged to the ground by connecting the back end part of the steel wire projecting from the back end of the guide wire 16 to the ground to prevent the radio-frequency heating of the guide wire 16. Thus, even if the front end part of the guide wire 16 should come into contact with the inner surface of the wall of, for example, the left superior pulmonary vein 101, there is no danger of excessively heating the wall of the left superior pulmonary vein 101. Since the front end part of the guide wire 16 projecting from the guide shaft 5 is formed of only the insulating material, the danger of excessively heating the wall of, for example, the left superior pulmonary vein 101 when the front end part of the guide wire 16 comes into contact with the inner surface of the wall of the left superior pulmonary vein 101 can surely be prevented even if the effect of grounding the back end part of the steel wire of the guide wire 16 is unsatisfactory.

Figure 5:
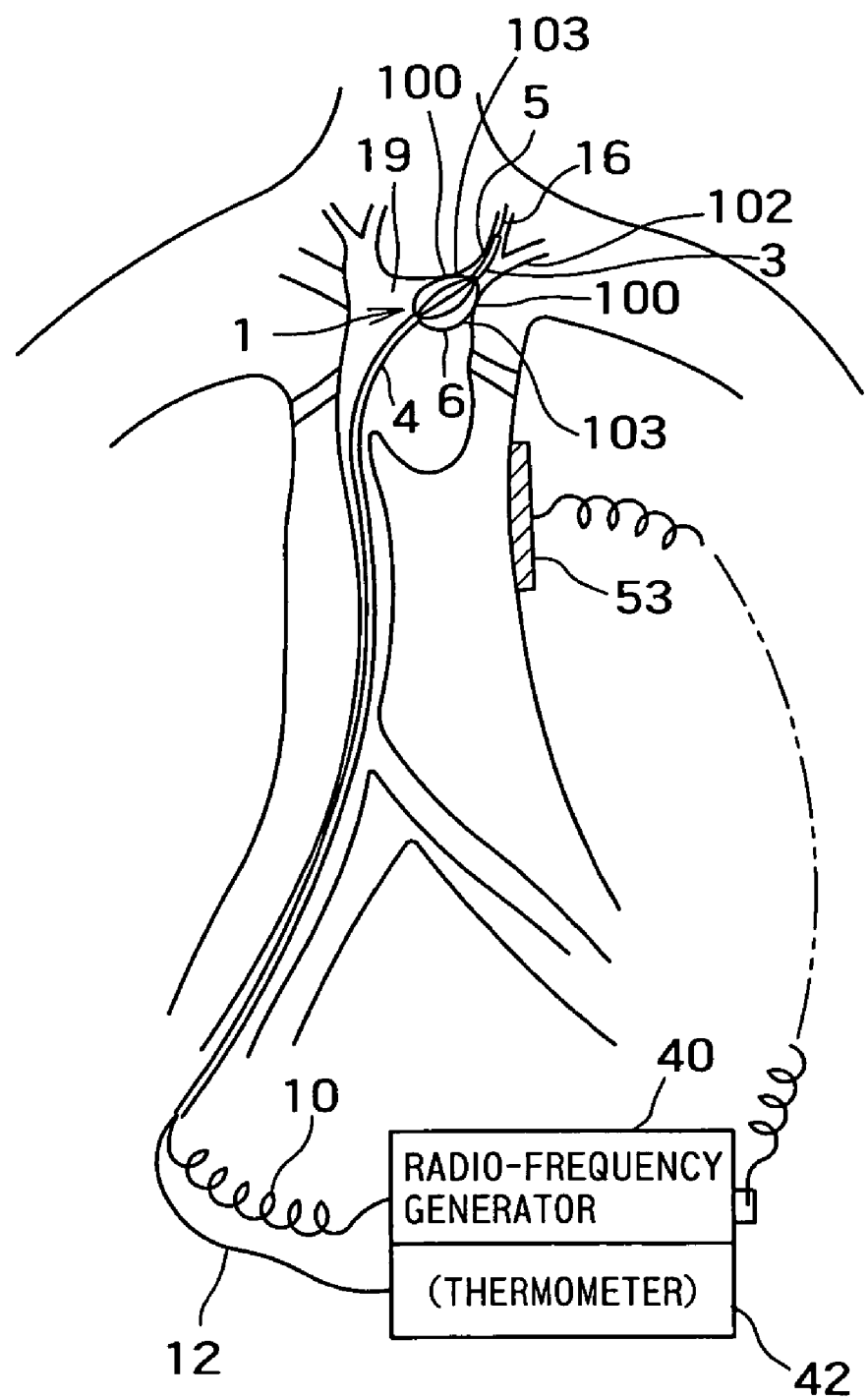
FIG. 5 is a view of assistance in explaining the use of a balloon catheter as a balloon for electrical isolation in a pulmonary vein for the treatment of atrial fibrillation.

As shown in FIG. 5, the lead wire 10 is wound helically. One end of the lead wire 10 is electrically connected to a radio-frequency power generator 40. Radio-frequency power generated by the radio-frequency power generator 40 is supplied through the lead wire 10 to the radio-frequency electrode 8. The balloon 6 has a large diameter to cauterize a target lesion 100 in the left atrial vestibule 103 having the opening greater than those of the pulmonary veins 101 and 102. Therefore, the radio-frequency power generator 40 needs to generate high radio-frequency power to heat the target lesion 100 at a desired temperature. For example, when the radio-frequency power of 13.56 MHz generated by the radio-frequency power generator 40 is supplied between the radio-frequency electrode 8 and a counter electrode 53 attached to the surface of the subject's body, and the diameter of the balloon 6 is about 2.5 cm, the radio-frequency power is in the range of 200 to 400 W. When the radio-frequency power is supplied between the radio-frequency electrode 8 and the counter electrode 53, tissues 18 in contact with the balloon 6 are cauterized by capacitive heating accompanied by radio-frequency dielectric heating. Pulmonary venous blood is sucked through the side holes 7 formed in the front end part 3a of the inner tube 3 or the guide shaft 5, and physiological saline water is discharged through the side holes 7 to cool the radio-frequency electrode 8 wound round the inner tube 3. Thus, temperature distribution inside the balloon 6 is made uniform. Consequently, the target lesion 100 in contact with the balloon 6 can uniformly be heated for cauterization.

The temperature of the liquid contained in the balloon 6 is sensed by the thermocouple 12 placed inside the inner tube 3. The thermocouple 12 is extended through the inner tube 3 and is connected to a thermometer 42 disposed outside the catheter tube 4. The thermometer 42 indicates the measured temperature of the liquid contained in the balloon 6. The radio-frequency power generator 40 is controlled so as to adjust the measured temperature of the liquid contained in the balloon 6 to a desired temperature.

The radio-frequency heating balloon catheter 1 in the first embodiment is provided with the guide shaft 5 extending from the front end part 3a of the inner tube 3, and the balloon 6 can be held on the target lesion 100 by placing the side surface 5a of the guide shaft 5 in contact with the inner surface of the wall of, for example, the left superior pulmonary vein 101. Thus, the inner surface of the wall of the left superior pulmonary vein 101 is never cauterized even if high radio-frequency power is supplied to cauterize the target lesion 100 in the left atrial vestibule 103, while it is possible that the inner surface of the wall of the left superior pulmonary vein 101 is cauterized when the balloon 6 is held on the target lesion 100 only by the guide wire 16. Thus, the target lesion 100 in the left atrial vestibule 103 can safely be cauterized with the balloon 6 held in a coaxial state.

When the interior of the atrium needs to be cauterized linearly to form a block line for the treatment of atrial flutter or atrial fibrillation, the block line can be formed by cauterizing the atrial vestibule 103 instead of individually cauterizing the openings of the superior pulmonary vein 101 and the inferior pulmonary vein 102. Thus, the four openings of the left superior pulmonary vein 101, the left inferior pulmonary vein 102, the right superior pulmonary vein 105 and the right inferior pulmonary vein 106 do not need to be individually cauterized. The number of parts to be cauterized can be reduced, for example, from four to two, and thereby time necessary for the ablation can be reduced.

Since the wall of the atrial vestibule 103, as compared with the walls of the pulmonary vein, is considerably thick, the atrial vestibule 103 does not contract easily when cauterized and hence the stenosis of the atrial vestibule 103 does not occur easily.

The cauterization of the posterior wall of the atrium in cauterizing the atrial vestibule 103 enhances the effect on the suppression of atrial fibrillation because the maintenance of atrial fibrillation requires an area in the posterior wall of the atrium not smaller than a certain fixed area and the cauterization of the atrial vestibule 103 reduces the area of the posterior wall of the atrium.

Since the guide wire 16 can be connected to the ground, the radio-frequency heating of the guide wire 16 can be prevented, and the excessive heating and electrification of the wall of, for example, the left superior pulmonary vein 101 can be prevented.

The radio-frequency electrode 8 wound round the inner tube 3 can be cooled by sucking pulmonary venous blood through the side holes 7 formed in the front end part 3a of the inner tube 3 or the guide shaft 5, and discharging physiological saline water through the side holes 7. Temperature distribution in the balloon 6 can be made uniform by stirring the liquid contained in the balloon 6 by a stirring mechanism 14, which will be described later. Thus, the target lesion 100 of a diameter in the range of, for example, 3 to 5 cm in contact with the balloon 6 can uniformly be cauterized.

A radio-frequency heating balloon catheter 1 in a second embodiment according to the present invention for heating pulmonary veins will be described with reference to FIGS. 3 and 4. The radio-frequency heating balloon catheter 1 in the second embodiment is provided with a temperature-distribution uniforming means for making uniform the temperature distribution in a liquid contained in a balloon 6.

In a conventional radio-frequency heating balloon catheter, an electrode placed in a balloon heats a liquid contained in the balloon ununiformly and thermal convection of the liquid occurs in the balloon. Consequently, the temperature distribution in the balloon unavoidably, becomes irregular and hence tissues in contact with the balloon cannot uniformly be heated. The radio-frequency heating balloon catheter 1 in the second embodiment is provided with a stirring mechanism 14 to stir the liquid contained in the balloon 6 so that the liquid contained in the balloon 6 may uniformly be heated so that tissues in contact with the balloon 6 can be hated as uniformly as possible by radio-frequency heating. As mentioned above, since high radio-frequency power is supplied to the balloon to cauterize the open ends of the pulmonary veins 103 and 106, the temperature distribution in the balloon 6 tends to be un-uniform. Therefore, the stirring mechanism 14 is very effective in making the temperature distribution in the balloon 6 uniform.

Figure 3:
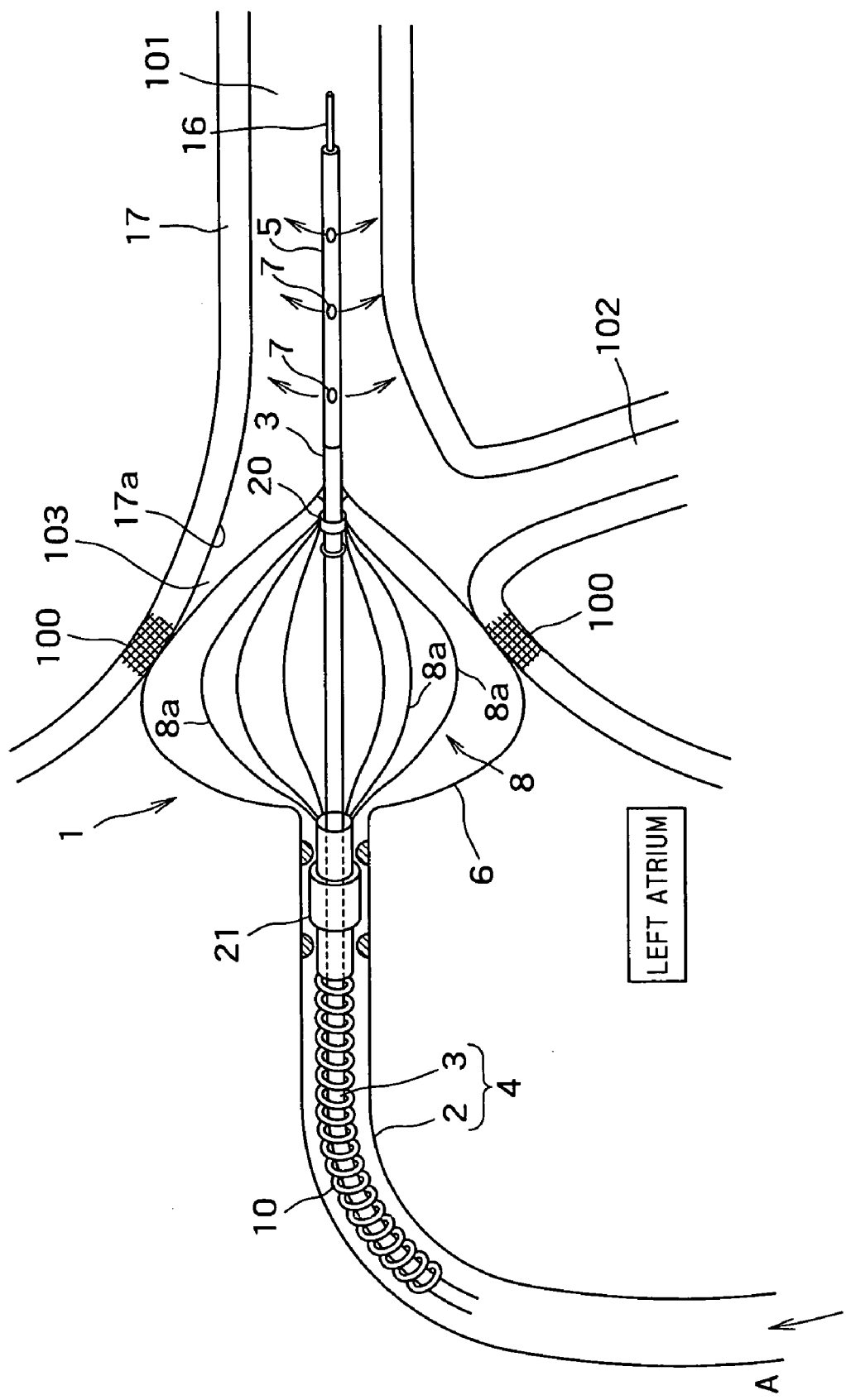
FIG. 3 a view of a part of a radio-frequency heating balloon catheter in a second embodiment according to the present invention.
Figure 4:
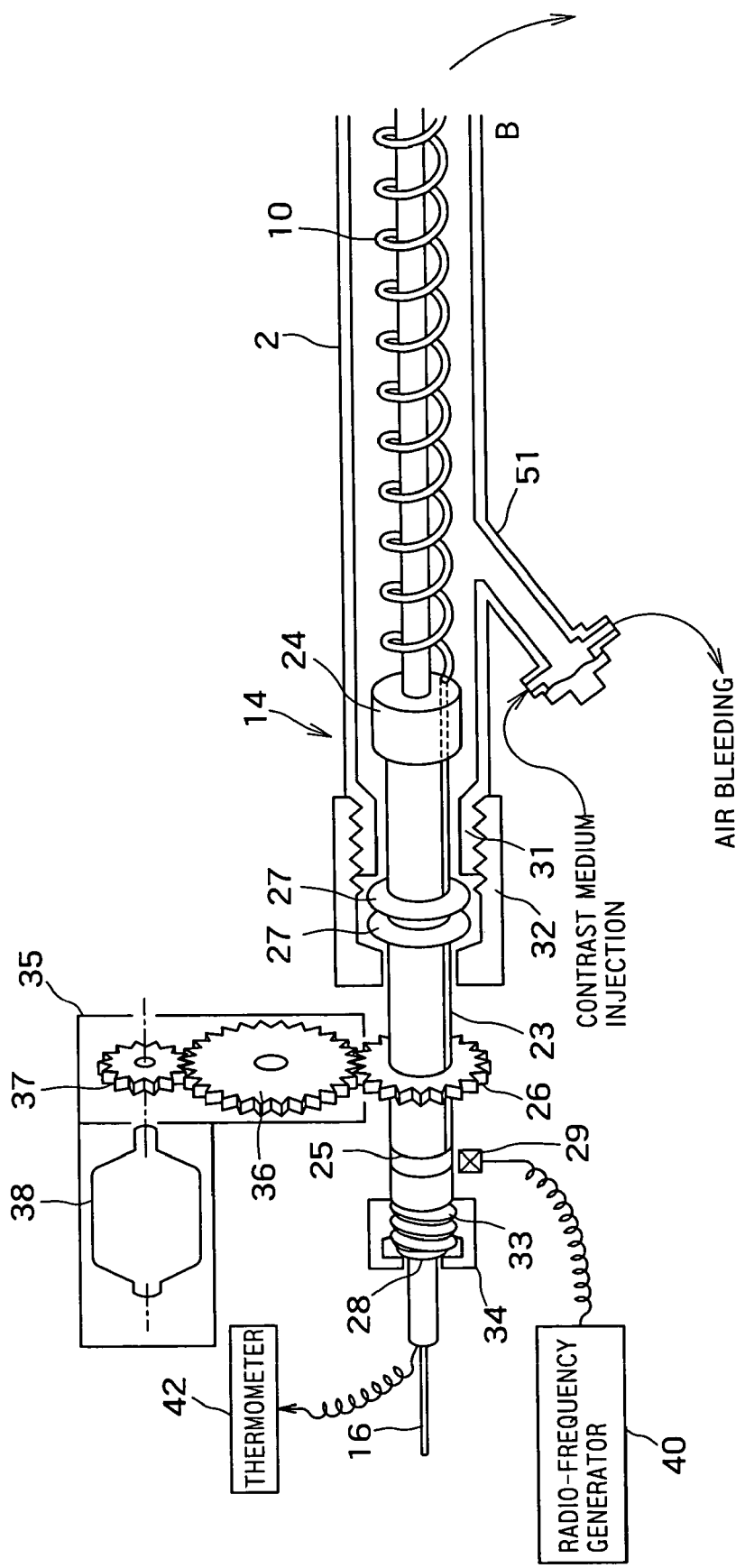
FIG. 4 a view of another part of the radio-frequency heating balloon catheter in the second embodiment to be connected to the right end of the part shown in FIG. 3.

Referring to FIGS. 3 and 4, in which the right end B of a view shown in FIG. 4 is joined to the left end A of a view shown in FIG. 3, the radio-frequency heating balloon catheter 1 comprises a catheter tube 4 including an outer tube 2 and an inner tube 3 slidable relative to the outer tube 2, an inflatable balloon 6 connected to the extremity of the outer tube 2 and a part near the extremity of the inner tube 3, and capable of coming into contact with a target lesion 100 when inflated, a radio-frequency electrode 8 disposed inside the balloon 6, a lead wire 10 electrically connected to the radio-frequency electrode 8, a thermocouple 12 placed in the balloon 6 to sense temperature in the balloon 6, a guide shaft 5 extending from a front end part 3a of the inner tube 3 and capable of holding the balloon 6 on the target lesion 100, a guide wire 16 extended through the catheter tube 4 and the guide shaft 5 to guide the catheter tube 4 and the guide shaft 5 to the target lesion 100, and a stirring mechanism 14 to make uniform the temperature distribution in the liquid contained in the balloon 6.

A front sleeve 20 is mounted on a front part, extending in the balloon 6, of the inner tube 3 so as to be turnable about the axis of the catheter tube 4. A back sleeve 21 is mounted on a front end part of the outer tube 2 so as to be turnable about the axis of the catheter tube 4.

The radio-frequency electrode 8 consists of a plurality of parallel splines 8a extended between the front sleeve 20 and the back sleeve 21. The straight splines 8a can be curved along the inner surface of the balloon 6 as shown in FIG. 3 when the inner tube 3 is slid relative to the outer tube 2 to inflate the balloon 6.

A base sleeve 23 is disposed near the back end of the outer tube 2 so as to be turnable about the axis of the catheter tube 4. A ring 24 is formed at the front end of the base sleeve 23, and a ring electrode 25 is attached to a part, near the back end, of the base sleeve 23. A driven gear 26 is mounted on a part, between the ring 24 and the ring electrode 25, of the base sleeve 23. A pantographic terminal 29 is disposed near the ring electrode 25 so as to be kept in contact with the ring electrode 25 when the ring electrode 25 rotates.

An external thread 31 is formed in a back end part of the outer tube 2. A flange 32 provided with an internal thread is screwed on the threaded back end part of the outer tube 2 so as to press O rings 27 against the back end of the outer tube 2. The O rings 27 are mounted loosely on the base sleeve 23 to permit the rotation of the base sleeve 23 and to prevent the leakage of a liquid through the gap between the inner surface of the outer tube 2 and the outer surface of the base sleeve 23. Thus, the leakage of a liquid through the gap between the base sleeve 23 and the outer tube 2, and the gap between the base sleeve 23 and the inner tube 3 can be sealed.

The inner tube 3 extends through the front sleeve 20, the back sleeve 21 and the base sleeve 23. An external thread 33 is formed in a back end part of base sleeve 23, and a flange 34 is screwed on the external thread 33 so as to press an O ring against the back end of the base sleeve 23. The O ring 28 seals the gap between the outer surface of the inner tube 3 and the inner surface of the base sleeve 23 to prevent the leakage of a liquid.

The lead wire 10 is wound helically round the inner tube 3. The lead wire 10 has one end connected to the back sleeve 21, and the other end connected to the ring 24 of the base sleeve 23 and the ring electrode 25. The terminal 29 in contact with the ring electrode 25 is connected electrically to a radio-frequency power generator 40. The radio-frequency power generator 40 supplies radio-frequency power through the lead wire 10 to the radio-frequency electrode 8.

The radio-frequency power generator 40 supplies radio-frequency power of, for example, 13.56 MHz between the radio-frequency electrode 8 and a counter electrode 53. For example, the radio-frequency power is in the range of 200 to 400 W when the diameter of the balloon 6 is about 2.5 cm.

A reduction gear 35 including gears 36 and 37, and a motor 38 is disposed near the driven gear 26. The motor 38 drives the driven gear 26 at a reduced rotating speed through the reduction gear 35 including the gears 36 and 37. The motor 38 may be controlled such that the output shaft of the motor 38 rotates in a single direction or may be controlled such that the output shaft rotates alternately in clockwise and counterclockwise directions for two full turns in each direction.

The lead wire 10 is formed of a material having a moderate rigidity. When the motor drives the base sleeve 23 for rotation through the driven gear 26, the rotative force of the motor 38 is transmitted to the lead wire 10 connected to the ring 24. Consequently, the back sleeve 21 and the front sleeve 20 are turned to turn the radio-frequency electrode 8.

The motor 38 turns the helical lead wire 10 by a predetermined number of full turns in a direction opposite the winding direction of the helical lead wire 10. When the driving force of the motor 38 is removed after thus turning the lead wire 10, the lead wire 10 turns of itself in the opposite direction to restore its original shape. Thus, the radio-frequency electrode 8 can be turned alternately in a clockwise direction and a counterclockwise direction by repetitively turning on and off the motor 38.

If the motor 38 is controlled so that its output shaft turns alternately, for example, two full turns in a clockwise direction and two full turns in a counterclockwise direction, the radio-frequency electrode 8 can alternately be turned clockwise and counterclockwise by using a straight lead wire 10 formed of an elastic material instead of the helical lead wire 10.

The stirring mechanism 14, i.e., a temperature-distribution uniforming means, for turning the radio-frequency electrode 8 comprises the front sleeve 20, the back sleeve 21, the base sleeve 23 and the motor 38.

As mentioned above, the lead wire 10 transmits both the rotative force of the motor 38 and the radio-frequency power generated by the radio-frequency power generator 40 to the radio-frequency electrode 8.

A branch tube 51 branches from a part, near the back end of the outer tube 2. The branch tube 51 is provided with a two-way valve to be used as an air bleed valve and a contrast medium injecting valve. The balloon 6 is evacuated through the air bleed valve of the branch pipe 51, and then a liquid, such as physiological saline water, for inflating the balloon 6 is supplied through the contrast medium injecting valve into the balloon 6.

The inner tube 3 has two lumens. One of the two lumens is used for containing the guide wire 16 and supplying a liquid medicine, and the other is used for containing a lead wire for transmitting information provided by the thermocouple 12, i.e., a temperature sensor.

The thermocouple 12 placed in the inner tube 3 senses the temperature of the liquid contained in the balloon 6. The thermocouple 12 is extended through the inner tube 3 and is connected to a thermometer 42 disposed outside the catheter tube 4. The thermometer 42 indicates the measured temperature of the liquid contained in the balloon 6.

The balloon 6 is formed of a heat-resistant, antithrombotic, elastic resin. The balloon 6 shown in FIG. 3 has the shape of a basket or an onion when inflated.

The radio-frequency electrode 8 consists of the several to several tens straight splines 8a extended between the front sleeve 20 and the back sleeve 21. The straight splines 8a can be curved by sliding the outer tube 2 and the inner tube 3 relative to each other to decrease the distance between the front sleeve 20 and the back sleeve 21 to form the radio-frequency electrode 8 in the shape of a basket or an onion. The change of the straight splines 8a between a straight shape and a curved shape can be ensured by forming the straight splines 8a of a shape memory alloy.

Front and left end parts of the splines 8a are coated with a resin to prevent the excessive radio-frequency heating of the front and the back end parts of the splines 8a.

Capacitive type radio-frequency heat can be generated between the radio-frequency electrode 8 and a counter electrode 53 (FIG. 5) attached to the surface of a subject's body when the radio-frequency power generator 40 generates radio-frequency power of, for example, 13.56 MHz.

The basket-shaped radio-frequency electrode 8 is connected to the ring electrode 25 on the base sleeve 23 by the helical lead wire 10, and the pantographic terminal 29 connected to the radio-frequency power generator 40 is kept in contact with the ring electrode 25 to supply radio-frequency power to the radio-frequency electrode 8. An electric field created by the turning radio-frequency electrode 8 is more uniform than that created by the fixed radio-frequency electrode 8.

The output rotating speed of the motor 38 is reduced by the reduction gear 35 and the lowered output rotating speed of the reduction gear 35 is transmitted through the driven gear 26 to the base sleeve 23. The rotation of the base sleeve 23 is transmitted to the back sleeve 21 by the lead wire 10 to turn the splines 8a in the balloon 6. The liquid filling up the balloon 6 is stirred by the turning splines 8a, so that irregular temperature distribution in the balloon 6 due to heat transfer by convection can be prevented and temperature is distributed uniformly in the balloon 6. The temperature of the liquid in a central part of the balloon 6, that of the liquid around the wall of the balloon 6 and that of tissues 18 in contact with the balloon 6 can be made substantially equal by thus stirring the liquid contained in the balloon 6. The temperature of the liquid in the central part of the balloon 6 is measured and is indicated by the thermometer 42, and the temperature indicated by the thermometer 42 can be considered to be the accurate temperature of the target lesion 100 in contact with the balloon 6.

Thus, the turning basket-shaped radio-frequency electrode 8 creates a high radio-frequency electric field, and stirs liquid contained in the balloon 6 to make uniform temperature distribution in the liquid contained in the balloon 6. Thus, the temperature of the target lesion 100 in contact with the balloon 6 can accurately be estimated.

Explanation will be made of the operation of the radio-frequency heating balloon catheter 1 used as a balloon catheter for electrical ablation for the treatment of atrial fibrillation in a pulmonary vein.

FIG. 5 is a view of assistance in explaining an operation for the ablation of a target lesion 100 in the open end of the left atrial vestibule 103.

An air-bleeding operation including injecting physiological saline water through the branch tube 51 of the outer tube 2 into the balloon 6 and discharging the physiological saline water from the balloon 6 through the branch tube 51 is repeated several cycles to bleed air from the balloon 6.

To insert the balloon catheter 1 in the left atrial vestibule 103, the balloon 6 is deflated and the inner tube 3 is slid to a limit position. Since the distance between the front sleeve 20 and the back sleeve 21 increases when the balloon catheter 1 is thus inserted in the left atrial vestibule 103, the splines 8a are extended straight and the balloon 6 is deflated in the smallest diameter. The thus deflated balloon 6 is inserted in the left atrial vestibule 103. The position of the balloon catheter 1 is adjusted to locate the balloon 6 near the target lesion 100, a contrast medium and physiological saline water are injected through the branch tube 51 into the balloon 6, and the inner tube 3 is pulled to inflate the balloon 6. Consequently, the distance between the front sleeve 20 and the back sleeve 21 decreases, and the splines 8a are curved to form a basket-shaped radio-frequency electrode 8 in the balloon 6. The fine adjustment of the position of the balloon catheter 1 is performed to bring the balloon 6 into contact with the target lesion 100.

Then, the motor 38 is actuated to transmit the rotative force of the motor 38 through the reduction gear 35 at lowered rotating speed to the base sleeve 23. The rotation of the base sleeve 23 is transmitted by the spiral lead wire extended through the catheter tube 4 to the back sleeve 21 connected to the front end of the inner tube 3. Consequently, the basket-shaped radio-frequency electrode 8 is turned in the balloon 6 to stir the liquids contained in the balloon 6.

Then, radio-frequency power of, for example, 13.56 MHz generated by the radio-frequency power generator 40 is supplied between a counter electrode 53 attached to the surface of a subject's body and the ring electrode 25 connected to the basket-shaped radio-frequency electrode 8 of the balloon catheter 1. The radio-frequency power is supplied through the terminal 29 in contact with the rotating ring electrode 25.

When a radio-frequency current flows through the basket-shaped radio-frequency electrode 8 turning in the balloon 6, capacitive heating accompanied by radio-frequency dielectric heating occurs for the radio-frequency heating of the balloon 6 and tissues 18 in contact with the balloon 6. The temperature of upper parts of the balloon 6 is higher than that of lower parts of the balloon 6 if thermal convection occurs in the balloon 6. Since the liquid contained in the balloon 6 is stirred by the basket-shaped radio-frequency electrode 8, temperature is distributed uniformly in the liquid.

If a fixed electrode is placed in the balloon 6, temperature is distributed ununiformly in the balloon 6 depending on the position of the fixed electrode. Since the radio-frequency electrode 8 turns in the balloon 6, a uniform radio-frequency electric field is created around the radio-frequency electrode 8. Consequently, the target lesion 100 in contact with the balloon 6 can uniformly be heated by radio-frequency heating as well as the interior of the balloon.

Although there is the possibility that the liquid around the sleeves 20 and 21 on which the splines 8a converge is heated excessively, such excessive heating of the liquid can be prevented by forming the sleeves 20 and 21 of a material having a low dielectric constant, such as a resin or a ceramic material, by coating pats of the splines 8a with a resin or by circulating cooling water through the inner tube 3.

Thus, the annular target lesion 100 in the opening of the left atrial vestibule 103 can uniformly be ablated, the left superior pulmonary vein 101 and the left inferior pulmonary vein 102 are electrically ablated to treat safely the atrial fibrillation originating from the pulmonary veins. The balloon catheter 1 in this embodiment is very useful to heat the liquid contained in the balloon 6 uniformly when the balloon 6 has a size suitable for treating the opening of the left atrial vestibule 103, and high radio-frequency power needs to be supplied to the balloon 6 having a large volume.

Figure 6:
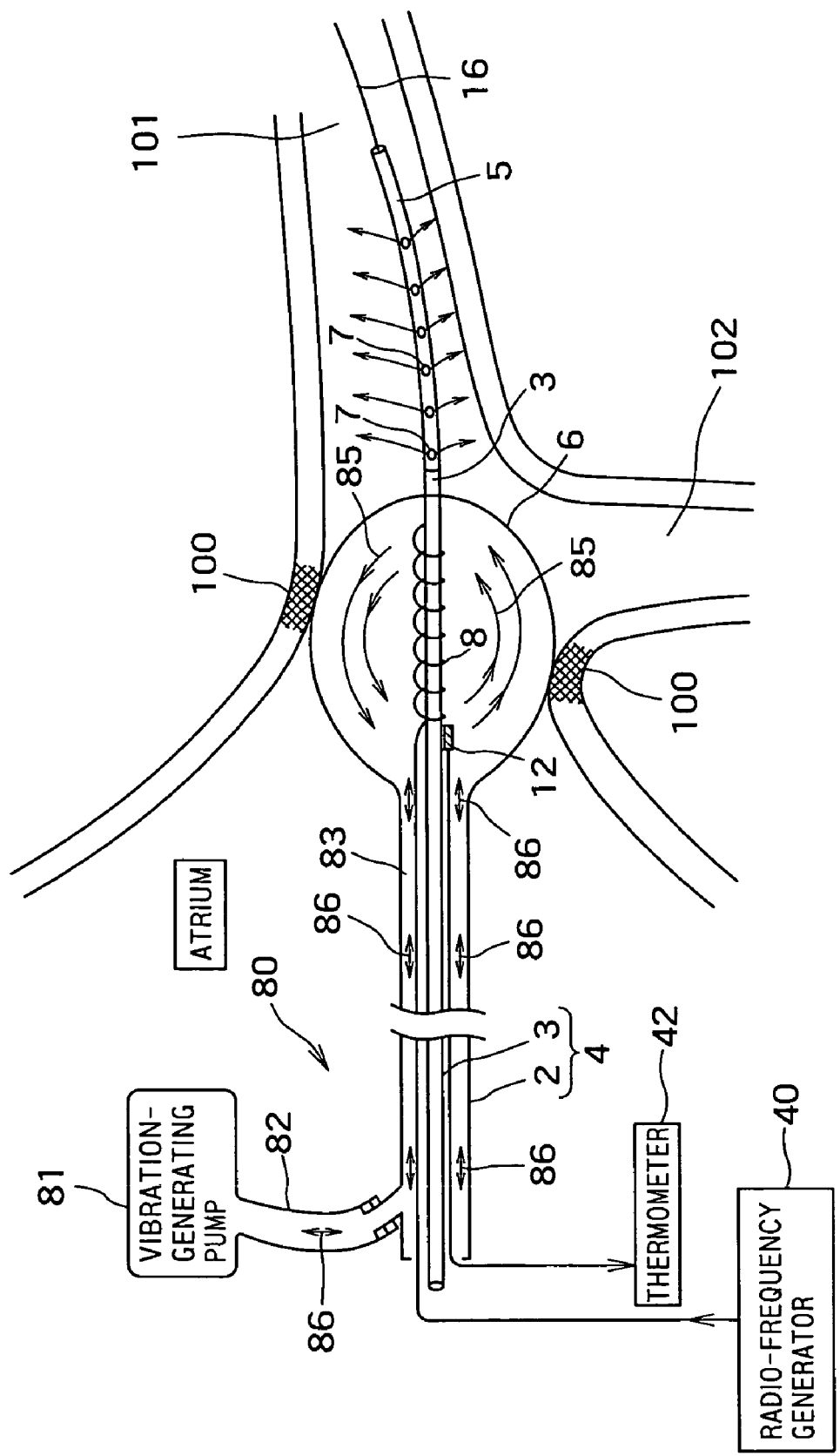
FIG. 6 is a view of a part of a radio-frequency heating balloon catheter in a third embodiment according to the present invention.
Figure 7:
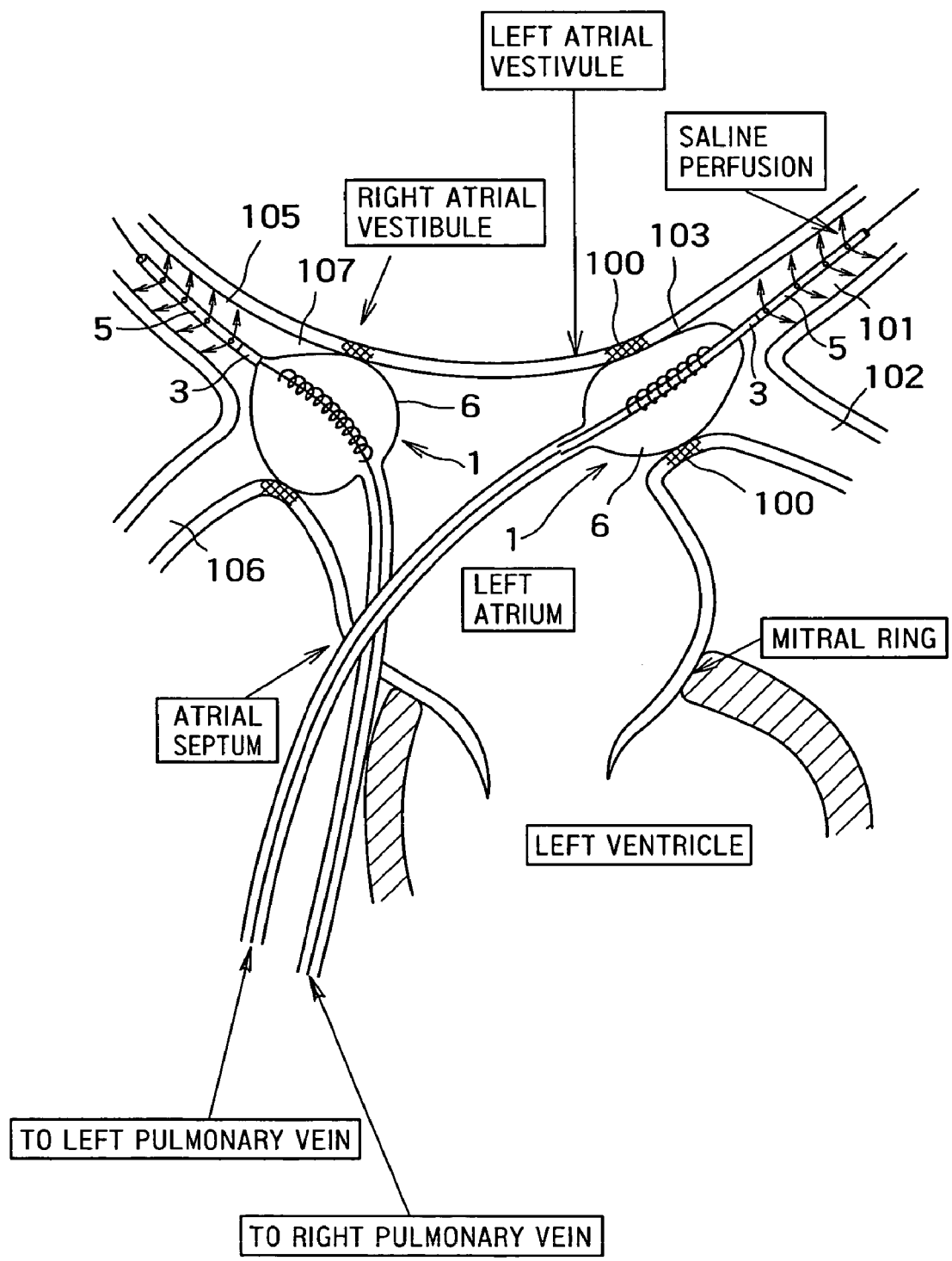
FIG. 7 is a view of assistance in explaining bringing a balloon into contact with an atrial vestibule formed by joining two pulmonary veins before the atrium.
Figure 8:
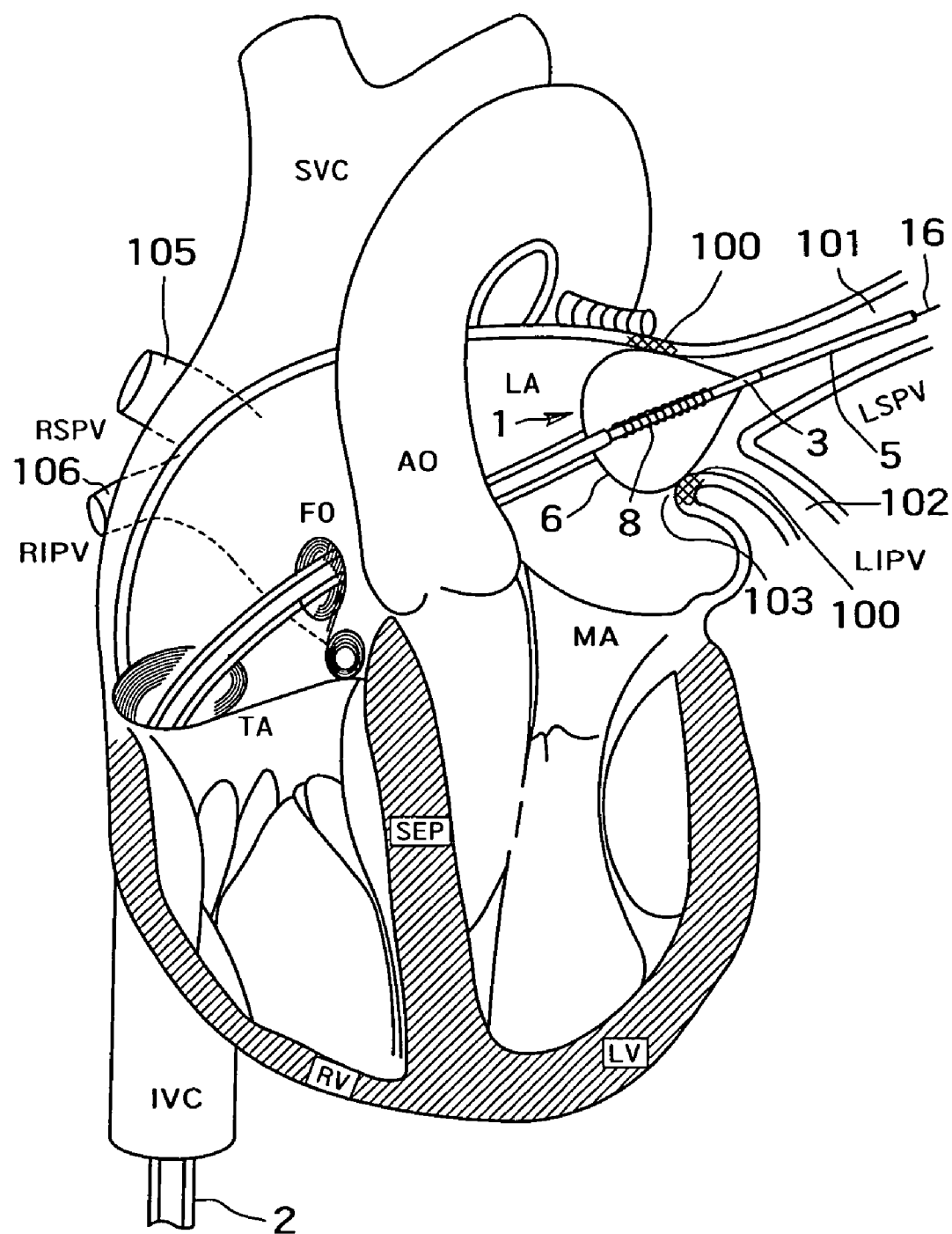
FIG. 8 is a view of an atrial vestibule at the junction between the superio and the inferior pulmonary vein before the atrial body found the inventors of the present invention.
Figure 9:
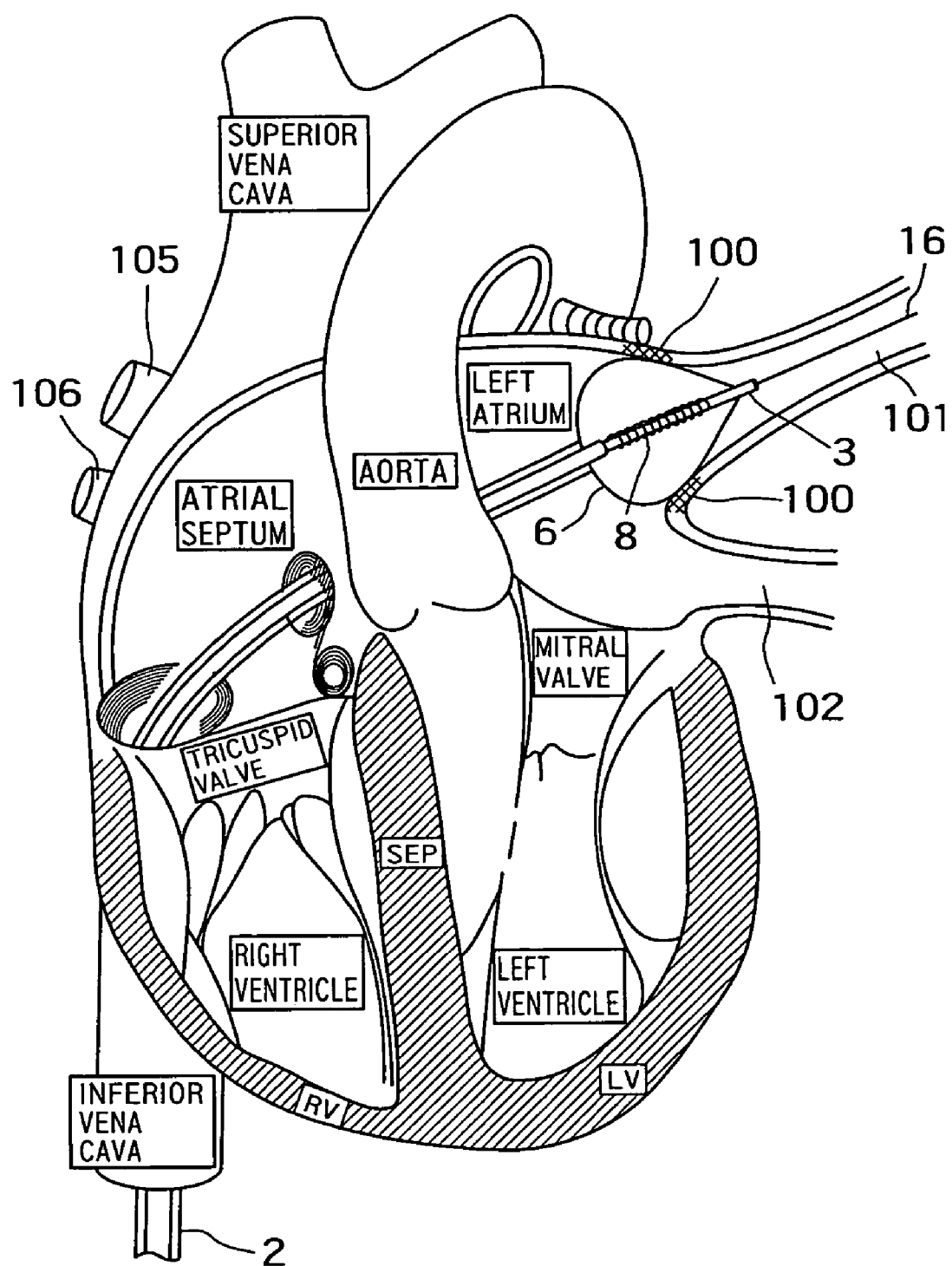
FIG. 9 is a view showing a balloon included in a conventional balloon catheter in contact with the open end of a single pulmonary vein.
Figure 10:
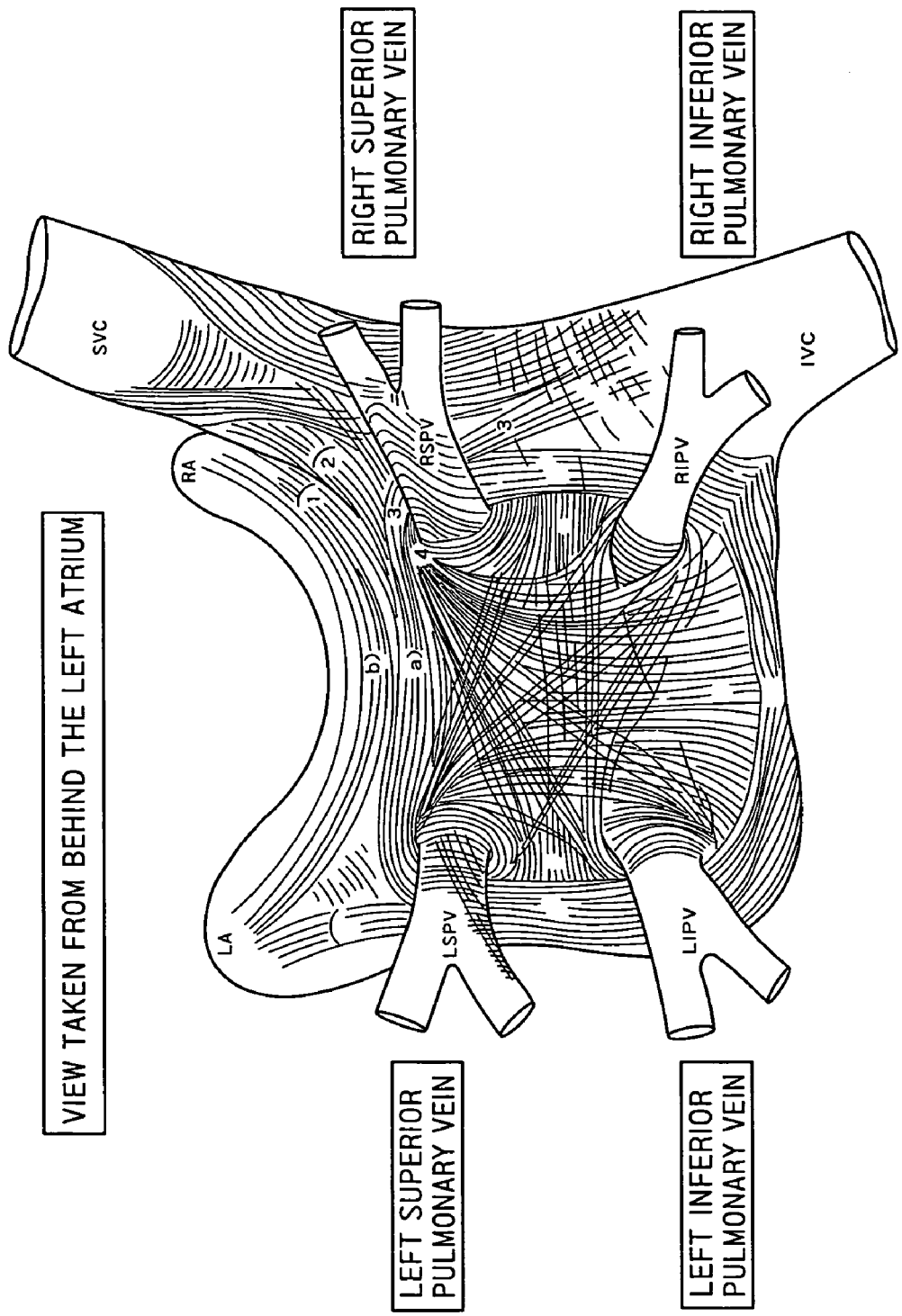
FIG. 10 is a view of assistance in explaining a formerly believed idea that the superior pulmonary veins and the inferior pulmonary veins connected to the right and the left atrium are separated and those four pulmonary veins open individually into the right and the left atrium.

A balloon catheter 1 in a third embodiment according to the present invention will be described with reference to FIG. 6. The balloon catheter 1 is provided with a stirring mechanism 80 for stirring a liquid contained in a balloon 6 to make temperature distribution in the balloon 6 uniform.

The stirring mechanism 80 includes a connecting pipe 82 communicating with a passage 83 defined by an outer tube 2 and an inner tube 3, and a vibration-generating device 81, such as a vibration-generating pump, capable of vibrating the liquid filling up the connecting pipe 82 and the passage 83. The connecting pipe 82 branches from the outer tube 2. The liquid fills up the connecting pipe 82, the passage 83 and the balloon 6. When vibrations of, for example, 1 Hz generated by the vibration-generating device 81 is applied to the liquid, an oscillatory wave 86 propagates through the liquid filling up the connecting pipe 82 and the passage 83. Consequently, random swirling currents 85 are generated in the liquid contained in the balloon 6 and there by temperature distribution in the liquid contained in the balloon 6 is made uniform. Thus, an atheroma formed in tissues 68 can be heated at an optimum temperature.

The vibration-generating device 81 may be a diaphragm pump having a vibrating diaphragm in contact with the liquid filling up the connecting pipe 82.

The oscillatory wave 86 generated by the vibration-generating device 81 is able to generate satisfactory swirling currents in the liquid contained in the balloon 6 by forming the balloon 6 of a material having a proper elasticity.

Although the stirring devices 14 and 80 are described by way of example as means for making the temperature distribution uniform, the means for making the temperature distribution uniform may be a circulating device for circulating the liquid through the balloon 6 to make uniform temperature distribution in the liquid contained in the balloon 6.

As apparent from the foregoing description, according to the present invention, the balloon can be held in contact with the target lesion in the atrial vestibule at the joint of the pulmonary veins by placing the side surface of the guide shaft extending from the extremity of the inner tube in contact with the inner surface of the pulmonary vein without excessively heating the inner surface of the pulmonary vein, the edges of the open ends of the four pulmonary veins do not need to be cauterized individually, and the atrial vestibule can be cauterized with the balloon held in a coaxial state.

Although the invention has been described in its preferred embodiments with a certain degree of particularity, obviously many changes and variations are possible therein. It is therefore to be understood that the present invention may be practiced otherwise than as specifically described herein without departing from the scope and spirit thereof.

What is claimed is:

1. A radio-frequency heating balloon catheter comprising:
    a catheter tube including an outer tube and an inner tube extending slidably through said outer tube;
    an inflatable balloon that is connected to an extremity of said outer tube and a part near an extremity of said inner tube and that is capable of coming into contact with a target lesion when inflated;
    a radio-frequency electrode serving as a counter to a surface electrode to be attached to a surface of a patient's body, said radio-frequency electrode being placed in a wall of said balloon or inside said balloon to supply radio-frequency power between said surface electrode and said radio-frequency electrode;
    a temperature sensor capable of sensing temperature inside said balloon;
    a guide shaft projecting from the extremity of said inner tube, said guide shaft being capable of holding said balloon on a target lesion; and
    a guide wire extending through said catheter tube and said guide shaft;
    wherein said guide shaft has a length such that a side surface of said guide shaft is able to contact an inner surface of a wall of a vein when said inflated balloon is in contact with a target lesion.

2. The radio-frequency heating balloon catheter of claim 1, wherein said guide shaft is formed of a nonconductive material having a low heat conductivity.

3. The radio-frequency heating balloon catheter of claim 2, wherein said guide shaft and said inner tube are formed integrally and coaxially of the same material.

4. The radio-frequency heating balloon catheter of claim 1, wherein said balloon is formed of a heat-resistant, anti-thrombotic, elastic material, and is formed in a shape such that said balloon is able to come into contact with an atrial vestibule at the junction between the superior and inferior pulmonary veins when inflated.

5. The radio-frequency heating balloon catheter of claim 4, wherein said guide shaft has a length such that the side surface of said guide shaft is able to come into contact with the superior or the inferior pulmonary vein when said inflated balloon is in contact with the atrial vestibule.

6. The radio-frequency heating balloon catheter of claim 4, wherein said balloon has a shape determined on the basis of data obtained by scanning the atrial vestibule by three-dimensional CT before executing ablation.

7. The radio-frequency heating balloon catheter of claim 1, wherein said guide shaft has a length longer than that of said balloon.

8. The radio-frequency heating balloon catheter of claim 1, wherein said guide shaft has a length between 1 and 10 cm.

9. The radio-frequency heating balloon catheter of claim 1, wherein a free end part of said inner tube or said guide shaft has side holes for suctioning blood in the pulmonary vein.

10. The radio-frequency heating balloon catheter of claim 1, wherein a back end of said guide wire is grounded.

11. The radio-frequency heating balloon catheter of claim 1, further comprising a temperature-distribution uniforming means for making uniform the temperature distribution in a liquid contained in said balloon.

12. The radio-frequency heating balloon catheter of claim 1, further comprising a cooling means for cooling said radio-frequency electrode.

13. The radio-frequency heating balloon catheter of claim 1, wherein the length of said guide shaft is such that when said inflated balloon is in contact with a target lesion of an atrial vestibule, a side surface of said guide shaft is in contact with an inner surface of a pulmonary vein.

14. The radio-frequency heating balloon catheter of claim 13, wherein said guide shaft is formed of a nonconductive material having a low heat conductivity.

* * * * *